United States Patent
Ehara et al.

(10) Patent No.: US 7,049,451 B2
(45) Date of Patent: May 23, 2006

(54) CARRIER OF CATALYST FOR PRODUCTION OF EPOXIDE, CATALYST FOR PRODUCTION OF EPOXIDE, AND METHOD FOR PRODUCTION OF EPOXIDE

(75) Inventors: Toshiya Ehara, Yokohama (JP); Hitoshi Takada, Yokohama (JP)

(73) Assignee: Nippon Shokubai, Co., Ltd., Osaka (JP)

( * ) Notice: Subject to any disclaimer, the term of this patent is extended or adjusted under 35 U.S.C. 154(b) by 48 days.

(21) Appl. No.: 10/406,772

(22) Filed: Apr. 3, 2003

(65) Prior Publication Data

US 2003/0191211 A1    Oct. 9, 2003

(30) Foreign Application Priority Data

Apr. 4, 2002  (JP) .............................. 2002-102148

(51) Int. Cl.
 *B01J 23/04*  (2006.01)
 *B01J 23/30*  (2006.01)
 *C07D 301/03* (2006.01)

(52) U.S. Cl. ...................... 549/534; 549/536; 502/347; 502/348

(58) Field of Classification Search ................ 549/534, 549/536; 502/347, 348
See application file for complete search history.

(56) References Cited

U.S. PATENT DOCUMENTS

| 3,908,002 | A | * | 9/1975 | Holler ......................... 423/628 |
| 4,039,561 | A |   | 8/1977 | Mitsuhata et al. ...... 260/348.34 |
| 4,136,063 | A | * | 1/1979 | Kimura et al. ............... 502/314 |
| 4,379,134 | A | * | 4/1983 | Weber et al. ................ 423/626 |
| 4,386,014 | A | * | 5/1983 | Gerberich et al. ........... 502/178 |
| 4,389,338 | A | * | 6/1983 | Mitsuhata et al. ........... 502/348 |
| 4,701,437 | A |   | 10/1987 | Boxhoorn et al. ........... 502/348 |
| 5,077,256 | A |   | 12/1991 | Yamamoto et al. .......... 502/243 |
| 5,502,020 | A | * | 3/1996 | Iwakura et al. .............. 502/317 |
| 5,801,114 | A | * | 9/1998 | Durand et al. ............... 502/302 |
| 5,801,259 | A | * | 9/1998 | Kowaleski ................... 549/536 |
| 6,313,325 | B1 | * | 11/2001 | Shima et al. ................ 549/534 |
| 6,600,056 | B1 | * | 7/2003 | Mikawa et al. .............. 549/534 |

FOREIGN PATENT DOCUMENTS

| GB | 1 373 489 | 11/1974 |
| JP | 55-145677 | 11/1980 |
| JP | 4-363139 | 12/1992 |
| WO | WO 00/14035 | 3/2000 |

OTHER PUBLICATIONS

Cary & Sundberg, Advanced Organic chemistry, 3rd Ed. pp. 359 (1990).*

* cited by examiner

*Primary Examiner*—Ceila Chang
*Assistant Examiner*—Raymond Covington
(74) *Attorney, Agent, or Firm*—Fish & Richardson P.C.

(57) ABSTRACT

A carrier for use in the catalyst for the production of an epoxide is obtained by preparing a carrier precursor containing (a) α-alumina, (b) silicon or a compound thereof, and (c) at least one element selected from the class consisting of germanium, tin, lead, phosphorus, antimony, and bismuth or a compound thereof and subsequently heat-treating the precursor in non-oxidative gas. The catalyst for the production of the epoxide is obtained by having silver deposited on this carrier and the epoxide is obtained from a corresponding unsaturated hydrocarbon of 2–4 carbon atoms with a high selectivity by using the catalyst.

23 Claims, No Drawings

CARRIER OF CATALYST FOR PRODUCTION OF EPOXIDE, CATALYST FOR PRODUCTION OF EPOXIDE, AND METHOD FOR PRODUCTION OF EPOXIDE

CROSS REFERENCE TO RELATED APPLICATIONS

Pursuant to 35 USC § 119, this application claims the benefit of Japan Patent Application No. 2002-102148 filed Apr. 4, 2002.

BACKGROUND OF THE INVENTION

1. Field of the Invention

This invention relates to a carrier of a catalyst for the production of an epoxide, a catalyst for the production of an epoxide, and a method for the production of an epoxide. More particularly, it relates to a carrier to be used for a catalyst for the production of an epoxide by subjecting a corresponding unsaturated hydrocarbon having 2 to 4 carbon atoms to gas phase partial oxidation with a molecular oxygen-containing gas, a catalyst for the production of an epoxide obtained by using this carrier, and a method for producing an epoxide by subjecting a corresponding unsaturated hydrocarbon having 2 to 4 carbon atoms to gas phase partial oxidation with a molecular oxygen-containing gas in the presence of this catalyst for the production of an epoxide.

2. Description of the Related Art

The catalyst for the production of an epoxide by the gas phase partial oxidation of a corresponding unsaturated hydrocarbon having 2 to 4 carbon atoms with a molecular oxygen-containing gas is required to possess high selectivity, high activity, and long life as the properties for performance. With the object of improving these properties, therefore, various studies have been made to date concerning carriers for catalysts for the production of epoxides, reaction promoters, conditions of heat treatment, and the like.

JP-A-55-145677, for example, discloses a silver catalyst which is obtained by depositing silver and optionally an alkali metal component or an alkaline earth metal component on a nonacidic carrier containing alumina, silica, and titania in a total concentration of not less than 99 mass % and metals of the groups of 5A, 6A, 7A, 8B, and 2B in the Periodic Table of the Elements (hereinafter designated as "IUPAC") in a total concentration of less than 0.1 mass % as reduced to metal oxides, having a pKa of +4.8, and not allowing methyl red to impart an acid color thereto and calcining the produced composite material in a current of air or hydrogen at a temperature in the range of 100°–1000° C.

U.S. Pat. No. 4,701,437 discloses a silver catalyst for the production of ethylene oxide which is characterized by using a carrier formed by adding 1–30 mass % of a tin compound to alumina.

JP-A-04-363139 discloses a silver catalyst for the production of ethylene oxide which is characterized by using a carrier obtained by adding a compound containing at least one element selected from the class consisting of the elements of the 3A–7A groups and the 3B–5B groups and the fourth, fifth, and sixth periods in the Periodic Table of the Elements to α-alumina and firing the resultant mixture.

U.S. Pat. No. 5,077,256 discloses a silver catalyst for the production of ethylene oxide which is obtained by precipitating silver and 0.001–0.05 gram-equivalent weight of a cesium compound as a reaction accelerator based on the weight of the perfected catalyst on a carrier having α-alumina as a main component and containing $3\times10^{-4}$–$2\times10^{-1}$ g of amorphous silica as reduced to Si atom per g of the carrier and subsequently subjecting the resultant composite material to a heat treatment in an inert gas containing oxygen at a concentration of not more than 3 vol. % at a temperature in the range of 400°–950° C.

The specification of U.S. Pat. No. 4,039,561 discloses the fact that the addition of Sb as a reaction promoters is effective when the addition is made during the preparation of a catalyst, not during the preparation of a carrier. The atomic ratio is not more than 0.15 of Sb to 100 of Ag.

U.S. Pat. No. 4,389,338 discloses a silver catalyst for the production of ethylene oxide, characterized by the catalyst being obtained by depositing silver and an alkali metal and/or thallium as a reaction accelerator on a carrier and subjecting the resultant composite material to a high-temperature heat treatment in an inert gas having an oxygen concentration of not more than 3% at a temperature in the range of 500°–950° C.

The aforementioned known catalysts for producing epoxides such as ethylene oxide are still deficient in such properties as selectivity. Thus, the desirability of further improving the properties of these catalysts has been finding recognition.

One object of this invention, therefore, is to provide an improved carrier for the production of an epoxide, specifically a carrier for the catalyst for the production of an epoxide, the carrier being such that the use thereof enables production of a catalyst excelling in such properties as selectivity.

Another object of this invention is to provide a catalyst for the production of an epoxide which excels in such properties as selectivity.

Still another object of this invention is to provide a method for the production of an epoxide which enables the epoxide to be produced industrially advantageously as by dint of high selectivity.

SUMMARY OF THE INVENTION

We, as a result of their study, have found that in the production of a carrier having α-alumina as a main component, the improved carrier for the production of an epoxide which is aimed at by this invention as described above is obtained by subjecting a carrier precursor containing (a) α-alumina, (b) silicon or a compound thereof, and (c) the element of antimony or a compound thereof to a heat treatment in a non-oxidative gas. The present invention has been perfected on the basis of this knowledge.

Specifically, this invention concerns a carrier to be used for the preparation of a catalyst for producing an epoxide by subjecting a corresponding unsaturated hydrocarbon having 2 to 4 carbon atoms to gas phase partial oxidation with a molecular oxygen-containing gas, which carrier is characterized by being obtained by preparing a carrier precursor containing (a) α-alumina, (b) silicon or a compound thereof, and (c) at least one element selected from the class consisting of germanium, tin, lead, phosphorus, antimony, and bismuth or a compound thereof and subsequently subjecting the precursor to a heat treatment in a non-oxidative gas.

This invention also concerns a catalyst having silver deposited on the carrier for the catalyst for the production of an expoxide and intended for the production of an epoxide by subjecting a corresponding unsaturated hydrocarbon having 2–4 carbon atoms to gas phase partial oxidation.

This invention further concerns a method for the production of an epoxide by subjecting a corresponding unsaturated hydrocarbon having 2–4 carbon atoms to gas phase partial oxidation with a molecular oxygen-containing gas in the presence of the catalyst for the production of an epoxide.

The catalyst for the production of an expoxide which is obtained by deposing a silver component on the carrier of this invention for the production of an expoxide possesses excellent properties and enables an epoxide to be produced with high selectivity by subjecting a corresponding unsaturated hydrocarbon having 2–4 carbon atoms to gas phase partial oxidation in the presence of the catalyst.

DESCRIPTION OF THE PREFERRED EMBODIMENT

As a carrier to be used in producing a catalyst for the production of ethylene oxide, the carrier having α-alumina as a main component and containing at least one element selected from the class consisting of the elements of the 4B group and the 5B group and the fourth-sixth periods in the Periodic Table of the Elements is disclosed in the JP-A-04-363139. In this official gazette, however, absolutely nothing is mentioned of a specific method for effecting this preparation of the carrier but the term "firing" is barely mentioned. This firing, therefore, is recognized to mean the ordinary firing which is performed in the air.

This invention is characterized by effecting the production of a carrier having α-alumina as a main component by preparing a carrier precursor containing (a) α-alumina, (b) silicon or a compound thereof, and (c) at least one element selected from the class consisting of germanium, tin, lead, phosphorus, antimony, and bismuth or a compound thereof and then heat-treating the precursor in a non-oxidative gas. The silver catalyst formed by depositing silver on the carrier so obtained is markedly excellent in terms of the selectivity of an epoxide as compared with the silver catalyst which is formed by depositing silver on a carrier obtained by effecting only the firing in the air as disclosed in the official gazette of JP-A-04-363139 (the examples and controls cited herein below available for reference).

The expression "unsaturated hydrocarbon having 2–4 carbon atoms" as used in this invention refers to ethylene, propylene, n- or iso-butylene, and 1,3-butadiene and the expression "epoxide obtained by subjecting the unsaturated hydrocarbon to gas phase partial oxidation" refers respectively to ethylene oxide, propylene oxide, n- or iso-butylene oxide, and 3,4-epoxy-1-butene. Among other unsaturated hydrocarbons cited above, ethylene and 1,3-butadiene prove particularly advantageous and ethylene proves most advantageous.

The term "carrier precursor" as used in this invention refers to (A) what is formed by causing at least one element selected from the group consisting of (c), germanium, tin, lead, phosphorus, antimony, and bismuth or a compound containing the element (hereinafter occasionally referred to as "additive element" or "additive compound") to be deposited by an operation of impregnation, for example, on a carrier having α-alumina as a main component, specifically a carrier suited to the preparation of a catalyst for the production of anepoxide and still awaiting deposition thereon of a silver component, (B) in the process of the (A), if it lacks a necessary amount of silicon or a compound thereof, silicon or a compound thereof is deposited at the same time that the element or the compound of (C) is deposited or before or after the deposition, and (C) what is formed by kneading α-alumina, an additive element and/or an additive compound, an inorganic and/or an organic binder generally used for the preparation of a carrier for use in a catalyst for the production of an epoxide, a pore forming agent, a thickening agent, etc. together with a proper amount of water, optionally molding the resultant blend, and thereafter firing the molded mass.

Incidentally, the carrier precursor mentioned above may contain therein such components as are used generally for improving a carrier, specifically such components as silica, titania, and silicon carbide which are usable as carrier materials and such components as alkali metals and alkaline earth metals which are usable for the purpose of improving a carrier in such amounts as avoid impairing the properties of the produced carrier for the catalyst for the production of an epoxide.

As typical examples of the raw material for α-alumina, not only α-alumina but also such aluminum compounds as γ-alumina, aluminumhydroxide, aluminumnitrate, and aluminum sulfate which are enabled by calcining to form α-alumina may be cited. Among other raw materials mentioned above, α-alumina proves particularly advantageous.

The α-alumina which is used for the preparation of the catalyst has an assay approximating to 98 mass %, preferably exceeding 98.5 mass % and has a sodium impurity content not exceeding about 0.06 mass %, specifically falling in the range of 0.02–0.06 mass %. The alumina comprises α-crystals having an average particle size preferably in the range of about 0.5—about 5 μm, preferably in the range of about 1 —about 4 μm. These crystals are preferred to sinter and form particles having an average particle diameter in the range of 30–100 μm, favorably in the range of 40–80 μm. The average size of such microcrystals has been decided by measuring the maximum sizes and the minimum sizes of a certain number of such microcrystals in the image of the transmission electron microscope (TEM) and averaging the results of the measurement. The α-alumina is present in the fired carrier in a quantity in the range of 90.0–99.9 mass %, preferably in the range of 92–99.6 mass %, based on the total mass of the carrier.

Silicon on the compound thereof (b) incorporated with the carrier precursor is added generally in the form of silica sol, silicon(elemental form) powder, silica powder, various siliates, etc. The amount thereof to be added is 0.01–10 mass %, preferably 0.1–5 mass %.

The element (c) to be incorporated in the carrier precursor mentioned above is at least one element selected from the group consisting of germanium, tin, lead, phosplhorus, antimony, and bismuth or a compound thereof. Among other substances mentioned above, antimony, phosphorus, and bismuth prove particularly advantageous and antimony proves more advantageous.

As the elements or compounds to be added, it is preferable to decide so as to be contained in a ratio of 0.001–5 mass %, preferably 0.01–4 mass % of metal element respectively in the carrier after heat treatment in no-oxidative atmosphere. If the cotent is out of the above-mentioned range, it is difficult to obtain the catalyst for producing the epoxide having excellent perfomance.

From of the compound to be added is not limited, and oxides, chlorides, nitrates and ammonium salt of the oxygen acid can be easily be slected considering the easiness of handling. For example, if the element to be added is various compounds such as antimony chloride, anitimony trioxide, anitomony pentoxide, various antimony sols, animony tartarate, antimony lactate, various alkalimetal hexahydroxoantimonate, etc. can be used.

Further, in case of antimony, it vaporized by heat treatment at a high temperature, so it is preferable to be decided the amount of use of antimony or antimony compound. If the amount is lesser, antimony component in the carrier becomes under 0.001 mass %, so the carrier of the catalyst for producing the epoxide cannot be obtained.

The following methods are available for the production of the carrier precursor.

(1) The carrier precursor is obtained by thoroughly kneading an α-alumina powder or an aluminum compound capable of forming an α-alumina powder and an organic and/or an inorganic binder such as silica sol, alumina sol, carboxymethyl cellulose, or corn starch and/or a complete combustion agent together with a proper amount of water, molding the resultant blend as by the technique of extrusion molding in a prescribed shape such as, for example, spheres or pellets, optionally subjecting the molded particles to a drying treatment, firing the dried particles (for example, at a temperature in the range of 1,000°–1,700° C., and preferably 1,200°–1,600° C.), impregnating the fired particles with a prescribed amount of the solution of the aforementioned additive element or the compound thereof, and drying the impregnated particles.

(2) The carrier precursor is obtained by thoroughly kneading an α-alumina powder or an aluminum compound capable of forming an α-alumina powder and an organic and/or an inorganic binder such as silica sol, alumina sol, carboxymethyl cellulose, or corn starch and/or a complete combustion agent together, and the aforementioned additive element or the compound thereof with a proper amount of water, molding the resultant blend as by the technique of extrusion molding in a prescribed shape such as, for example, spheres or pellets, optionally drying the formed particles, and firing the dried particles.

The binder facilitates the step of extrusion by imparting a lubricating property. Typical examples of the binder include a combination of alumina gel with such a peptizer as nitric acid or acetic acid. Suitable binders embrace such carbon-based materials are capable of acting as a perfect combustion agent. Preferable organic binders are cellulose, substituted celluloses (such as methyl cellulose, ethyl cellulose, and carboxyethyl cellulose), organic stearic esters (such as, for example, methyl and ethyl stearates), waxes, and polyolefin oxides may be cited. Preferred binders are methyl cellulose and starch.

The perfect combustion agent is a material which is so incorporated in the mixture that it may be perfectly removed from the carrier in the process of firing and consequently enabled to leave controlled pores behind in the carrier. The materials answering this description include coke, carbon powder, graphite, powdered plastics (such as of polyethylene, polystyrene, and polycarbonate), rosin, cellulose and cellulosic materials, sawdust, and carbon-based materials such as ground fruit shells (such as shells of pecan, cashew, nut, apricot, and hazel nut), and other plant materials. A varying type of carbon-based binder also can serve as a perfect combustion agent. The perfect combustion agent is supplied in such a quantity and a size distribution as affords a final carrier exhibiting a pore volume preferably in the range of about 10–80 cc/g and more preferably in the range of 30–70 cc/g. A preferred perfect combustion agent is a material originating in the cellulose such as of ground hard fruit shell.

The carrier precursor obtained as described above is heat-treated in the atmosphere of a non-oxidative gas.

The term "non-oxidative gas" as used in this invention refers to a gas which may contain oxygen in a concentration not exceeding 10 vol. %. As typical examples of the non-oxidative gas, (A) a reducing gas, (B) an inert gas, and (C) a gas having an oxygen concentration of not more than 10 vol. %, preferably not more than 3 vol. % may be cited.

As typical examples of the aforementioned (A) reducing gas, hydrogen gas, carbon monoxide gas, nitrogen monoxide gas, dinitrogen oxide gas, ammonia gas, and mixtures of such gases with an inert gas may be cited. As typical examples of the inert gas, not only nitrogen gas and argon gas but also rare gases, carbon dioxide gas, and alkane gases may be cited. It is allowable to use such an inert gas as avoids inducing an unwanted reaction with hydrogen gas or carbon monoxide gas when subjected to a heat treatment. Among other gases mentioned above, the mixture of hydrogen gas and nitrogen gas can be advantageously used. The hydrogen gas concentration in this mixture is in the range of 0.1–50 vol. %, preferably 0.1–15 vol. %, and more preferably 0.1–10 vol. %.

As typical examples of the aforementioned (B) inert gas, not only nitrogen gas and argon gas but also rare gases, carbon dioxide gas, and alkane gases may be cited.

As a typical example of the aforementioned (C) gas having an oxygen concentration of not more than 10 vol. %, the mixture of not more than 10 vol. % of oxygen and an inert gas may be cited. As concrete example of the inert gas which is usable in the mixture, not only nitrogen gas and argon gas but also rare gases, carbon dioxide gas, and alkane gases may be cited. It is also permissible to use a gas obtained by diluting the air with nitrogen gas to an oxygen concentration of not more than 10 vol. % and a gas obtained by deriving the air of oxygen to an oxygen concentration of not more than 10 vol. %.

Among other gases mentioned above, the mixture consisting of hydrogen gas and nitrogen gas and specifically having a hydrogen gas concentration in the range of 0.1–10 vol. % is used particularly advantageously.

The heat treatment is properly carried out at a temperature in the range of 400°–1700° C., preferably 450°–1500° C. If the temperature of the heat treatment deviates from the range specified above, the carrier for use in a catalyst for the production of an epoxide, i.e. the target of this invention, will not be attained.

The shape of the carrier of this invention for use in the catalyst for the production of an epoxide does not need to be particularly restricted but may be properly selected from among shapes of carrier such as, for example, rings, saddles, spheres, and pellets which are generally used for the preparation of a catalyst for the production of an epoxide in consideration of such industrial points as pressure loss and strength.

BET (Brunauer—Emmett—Teller) specific surface area of the carrier for the catalyst contemplated by this invention is generally in the range of 0.1–10 $m^2/g$, preferably in the range of 0.3–5 $m^2/g$, and more preferably in the range of 0.5–2 $m^2/g$. If the specific surface area is unduly low, the shortage will result in preventing acquisition of a fully satisfactory coefficient of water absorption and rendering difficult the deposition of a catalyst component because the sintering proceeds excessively. Conversely, if the specific surface area is unduly high, the excess will result in decreasing the diameter of pores and accelerating the secondary oxidation of ethylene oxide. The water absorption ratio is generally in the range of 10–50%, preferably in the range of 20–50%. If the water absorption ratio is unduly low, the shortage will result in rendering the deposition of a catalyst component difficult. Conversely, if the water absorption ratio is unduly high, the excess will result in preventing the carrier from acquiring fully satisfactory strength. The mean pore diameter is generally in the range of 0.1–5 μm, preferably in the range of 0.2–3 μm, and more preferably in the range of 0.3–0.9 μm. If the mean pore diameter is unduly large, the excess will result in lowering the strength. Conversely, if the mean pore diameter is unduly small, the shortage will result in accelerating the successive oxidation of ethylene oxide owing to the stagnation of the gas. The porosity is generally in the range of 20–80% and preferably in the range of 40–75%. If the porosity is unduly low, the shortage will result in excessively enlarging the packing density of the carrier. Conversely, if the porosity is unduly high, the excess will result in preventing the carrier from acquiring fully satisfactory strength.

The average equivalent diameter of the carrier mentioned above is generally in the range of 3–20 mm, preferably 5–10 mm.

The catalyst using carrier of this invention for the production of an epoxide can be prepared by effecting deposition of silver and optionally a reaction promoter on a carrier by any of the methods generally adopted for the preparation of a silver catalyst of the class under discussion with the exception of using as such a carrier of this invention obtained as described above and used for the catalyst of this invention for the production of an epoxide.

Specifically, this preparation has only to be implemented by forming a uniformly dispersing complex in an aqueous solution of a silver compound and a complex-forming agent, preferably adding such a reaction promoter as cesium to the resultant dispersion, impregnating the carrier of this invention with the produced mixed liquid, and activating the impregnated mixed liquid to induce deposition of silver on the composite carrier. As typical examples of the silver compound, various silver salts such as silver oxalate, silver acetate, silver carbonate, silver sulfate, and silver chloride may be cited. Among other silver salts mentioned above, silver oxalate is used particularly advantageously. As typical examples of the complex-forming agent, various species of amines such as ethanol amine and ethylene diamine may be cited. The activating temperature is in the range of 120°–700° C., preferably 120°–600° C., and more preferably 150°–500° C. The amount of silver to be deposited is generally in the range of 1–30 mass %, preferably 5–20 mass.

When at least one element selected from the group consisting of alkali metals such as lithium, potassium, rubidium, and cesium and thallium is used as the reaction promoter, the total quantity of the reaction promoter is generally in the range of 0.0001–5 mass % (calculated as oxide $M_2O$), preferably in the range of 0.001–3 mass %, more preferably in the range of 0.01–2 mass %, and still more preferably in the range of 0.1–1 mass %, based on the total mass of the catalyst.

The amount of silver to be deposited is generally in the range of 5–30 mass %, and preferably 5–20 mass %. If the amount of silver to be deposited is unduly low, the shortage will bring an adverse effect on the life of the catalyst because of a decrease in the active sites due to sintering of silver. Conversely, if this amount is unduly large, the excess will accelerate sequential oxidation of epoxide because the silver undergoes serious sintering and blocks pores during the course of the reaction. Thus, the deviation of this amount in either way from the range is unfavorable.

In the catalyst of this invention for the production of an epoxide, the silver catalyst for the production of ethylene oxide intended for the production of ethylene oxide by gas phase partial oxidation of ethylene and formed by depositing silver on a carrier using α-alumina as a main component, specifically the catalyst for the production of ethylene oxide which is formed by using as the carrier what is obtained by preparing a carrier precursor containing α-alumina and antimony or an antimony compound and subsequently subjecting this precursor to a heat treatment in a mixed gas of hydrogen and an inert gas at a temperature in the range of 400–1700° C. proves particularly advantageous.

The reaction for producing an epoxide by subjecting a corresponding unsaturated hydrocarbon of 2–4 carbon atoms to gas phase partial oxidation with a molecular oxygen-containing gas by the use of the aforementioned catalyst for production of epoxide can be carried out by following any of the methods generally adopted for the reactions of this sort. For the purpose of producing ethylene oxide from ethylene, for example, the reaction gas comprising 1–40 vol. % of ethylene, 1–20 vol. % of oxygen, and 1–20 vol. % of carbon dioxide gas, also containing methane, ethane, or nitrogen gas generally used as a ballast gas, and further containing an alkyl chloride such as ethyl chloride, ethylene dichloride, vinyl chloride, or methyl chloride added for repressing excessive oxidizing activity is only required to contact the catalyst of this invention for the production of an epoxide under a pressure in the range of 0.1–3.5 MPa at a temperature in the range of 180–300° C., preferably 200–270° C. Incidentally, the amount of the alkyl chloride to be added is preferred to be in the range of 0.1—several 10's ppm. The addition of the alkyl chloride markedly improves the selectivity, though the activity is impaired somewhat. The space velocity in the reaction is in the range of 1,000–30,000 $hr^{-1}$ (STP), preferably 3,000–8,000 $hr^{-1}$ (STP).

Incidentally, the ethane content in the residual gas mentioned above is preferably not more than 3 vol. % and advantageously not more than 0.5 vol. %.

The organic halogen compound content in the residual gas is preferably not more than 100 ppm and advantageously not more than 10 ppm.

As one typical example of the use of the carrier of this invention for the production of an epoxide, the use in a silver catalyst for the production of 3,4-epoxy-1-butene by the gas phase oxidation of 1,3-butadiene may be cited. It is generally known that this silver catalyst is obtained by depositing a silver component on a carrier such as of α-alumina or silica. As this carrier, the carrier contemplated by this invention can be used advantageously.

The catalyst for the production of 3,4-epoxy-1-butene can be prepared by following any of the well-known methods while using the carrier of this invention. By the same token, the production of 3,4-epoxy-1-butene by the gas phase oxidation of 1-3-butadiene can be implemented by following any of the well-known methods while using as the catalyst therefor the catalyst of this invention for the production of an epoxide.

Now, this invention will be described more specifically below with reference to working examples adduced herein.

Incidentally, the amount of the additive element (such as, for example, antimony) in the completed carrier was determined by the XRF measurement (assayed by the FP method using an instrument made by Kabushiki Kaisha Rigaku and sold under the product code of "RIX-2000"). The degree of conversion of ethylene and the selectivity of the reaction for ethylene oxide were calculated in accordance with the following formulas. (The same will apply to other unsaturated hydrocarbons herein below.)

Conversion of ethylene (%)=[(Number of mols of ethylene before reaction−Number of mols of ethylene after reaction)/(Number of mols of ethylene before reaction)]×100

Selectivity to ethylene oxide (%)=[(Number of mols of ethylene converted to ethylene oxide)/(Number of mols of ethylene consumed by reaction)]×100

EXAMPLE 1

An alumina carrier having α-alumina as a main component (composed of 96 mass %, 2.6 mass % of silica, and 1.4 mass % of other components and having a BET specific surface area of 1.2 m²/g, a water absorption ratio of 40%, and an apparent porosity of 61%) was obtained by thoroughly kneading 900 g of an α-alumina powder (having an average primary particle diameter of 1.5 μm and an average secondary particle diameter of 45 μm), 250 g of 10% silica sol, 250 g of 20% alumina sol, 50 g of carboxymethyl cellulose, 50 g of corn starch, and 100 g of crushed apricot shell with 200 g of water, extrusion molding the resultant blend, then cutting the extruded threads of blend into pellets, drying the pellets, and firing the dried pellets in the air at 1400° C. A carrier precursor was obtained by impregnating the alumina carrier with 10% antimony sol (made by Nissan Chemicals Industries, Ltd. and sold under the product code of "A-1510LP") diluted with such an amount of water as to adjust the concentration thereof to 1.37 mass % as reduced to metal (based on the mass of the alumina carrier) over a water bath, and then drying the impregnated carrier.

A complete carrier was obtained by subjecting the carrier precursor to a heat treatment performed in a current of the mixture of 4 vol. % of hydrogen gas and 96 vol. % of nitrogen gas by increasing temperature from the room temperature to 1200° C. at a temperature increasing rate of 10° C./min. and retaining the temperature of 1200° C. for two hours and thereafter allowing the heated carrier precursor to cool to the room temperature. The water absorption ratio and the apparent porosity of this completed carrier were as shown in Table 1. Incidentally, the specific surface area of the carrier showed virtually no change before and after the heat treatment.

The completed carrier was washed with boiling purified water. On this completed carrier measuring 80 ml. in volume, silver and cesium as a promoter were deposited. Specifically, a silver catalyst was obtained by adding 14 ml of ethanol amine and 0.064 g of cesium nitrate to 16.6 g of silver oxalate and further adding purified water thereto to form a uniform solution, impregnating the completed carrier with the solution over a water bath, drying the impregnated carrier, and subjecting the dried carrier to an activating treatment in a current of air at 200° C. for 10 minutes and at 400° C. for 10 minutes.

A reaction vessel measuring 3 mm in inside diameter was packed with the silver catalyst pulverized in advance to 600–850 μm. A reaction gas composed of 23 vol. % of ethylene, 7.5 vol. % of oxygen, 7 vol. % of carbon dioxide gas, 5 ppm of ethyl chloride, and the balance of methane as a ballast gas was passed through the reaction vessel and allowed to undergo such a reaction under a pressure of 2.4 MPa at a space velocity of 5500 hr$^{-1}$ as to set the conversion of ethylene at 11%. The treated gas was assayed to determine the selectivity of the reaction for ethylene oxide. The results were as shown in Table 1.

EXAMPLE 2

A carrier precursor was obtained by thoroughly kneading 900 g of an α-alumina powder (having an average primary particle diameter of 1.5 μm and an average secondary particle diameter of 45 μm), 250 g of 10% silicasol, 250 g of 20% alumina sol, 137 g of 10% antimony sol (made by Nissan Chemicals Industries, Ltd. and made under the product code of "A-1510 LP), 50 g of carboxymethyl cellulose, 50 g of corn starch, and 100 g of crushed apricot shell with 200 g of water, extrusion molding the resultant blend, then cutting the extruded threads of blend into pellets, drying the pellets, and then firing the dried pellets in the air at 1400° C. This carrier precursor equaled the carrier precursor of Example 1 in the amount of antimony added and substantially equaled it in such other factors as specific surface area, whereas it differed therefrom in respect that the addition of antimony was made while the α-alumina powder, sols and soon were being kneaded.

Thereafter, a complete carrier was produced by performing the same heat treatment as in Example 1 while using the aforementioned carrier precursor, a silver catalyst was produced by effecting deposition of silver on the complete carrier in the same manner as in Example 1, and gas phase oxidation of ethylene was carried out by the use of the silver catalyst in the same manner as in Example 1 to determine the selectivity of the reaction for ethylene oxide. The results were as shown in Table 1.

EXAMPLE 3

Gas phase oxidation of ethylene was carried out by following the procedure of Example 1 while using the mixture consisting of 1.5 vol. % of oxygen gas and 98.5 vol. % of nitrogen gas during the heat treatment and the reaction was tested to determine the selectivity of the reaction for ethylene oxide. The results were as shown in Table 1.

EXAMPLE 4

A complete carrier was produced by performing a heat treatment in the same manner as in Example 1 while using a carrier precursor prepared by following the procedure of Example 2 while adding 15 g of germanium dioxide in the place of antimony sol, a silver catalyst was produced by effecting deposition of silver on the complete carrier in the same manner as in Example 1, and gas phase oxidation of ethylene was carried out by using the silver carrier in the same manner as in Example 1 and the reaction was tested to determine the selectivity of the reaction for ethylene oxide. The results were as shown in Table 1.

EXAMPLE 5

A complete carrier was produced by performing a heat treatment in the same manner as in Example 1 while using a carrier precursor prepared by following the procedure of Example 2 while adding 13 g of tin dioxide in the place of antimony sol, a silver catalyst was produced by effecting deposition of silver on the complete carrier in the same manner as in Example 1, and gas phase oxidation of ethylene was carried out by using the silver catalyst in the same manner as in Example 1 and the reaction was tested to determine the selectivity of the reaction for ethylene oxide. The results were as shown in Table 1.

EXAMPLE 6

A complete carrier was produced by performing a heat treatment in the same manner as in Example 1 while using a carrier precursor prepared by following the procedure of Example 2 while adding 12 g of lead dioxide in the place of antimony sol, a silver catalyst was produced by effecting deposition of silver on this complete carrier in the same manner as in Example 1, and gas phase oxidation of ethylene was carried out by using the silver catalyst in the same manner as in Example 1 and the reaction was tested to determine the selectivity of the reaction for ethylene oxide. The results were as shown in Table 1.

EXAMPLE 7

A complete carrier was produced by performing a heat treatment in the same manner as in Example 1 while using a carrier precursor prepared by following the procedure of Example 2 while adding 55 g of aluminum phosphate hydrate in the place of antimony sol, a silver catalyst was produced by effecting deposition of silver on the complete carrier in the same manner as in Example 1, and gas phase oxidation of ethylene was carried out by using the silver catalyst in the same manner as in Example 1 and the reaction was tested to determine the selectivity of the reaction for ethylene oxide. The results were as shown in Table 1.

EXAMPLE 8

A complete carrier was produced by performing a heat treatment in the same manner as in Example 1 while using a carrier precursor prepared by following the procedure of Example 2 while adding 24 g of bismuth pentoxide in the place of antimony sol, a silver catalyst was produced by effecting deposition of silver on the complete carrier in the same manner as in Example 1, and gas phase oxidation of ethylene was carried out by using the silver catalyst in the same manner as in Example 1 and the reaction was tested to determine the selectivity of the reaction for ethylene oxide. The results were as shown in Table 1.

EXAMPLE 9

A carrier precursor was obtained by washing an alumina carrier (made by Norton Corp. and sold under the product code of "SA-5552") in boiling purified water, impregnating the washed alumina carrier with a 10% antimony sol (made by Nissan Chemicals Industries, Ltd. and sold under the product code of "A-1510LP") diluted with such an amount of water as to adjust the concentration thereof to 1.37 mass % as reduced to metal (based on the mass of alumina carrier) over a water bath, and then drying the impregnated carrier.

Silver and cesium as a promoter were deposited on 80 ml of the completed carrier. On this completed carrier measuring 80 ml in volume, silver and cesium as a promoter were deposited. Specifically, a silver catalyst was obtained by adding 14 ml of ethanol amine and 0.03 g of cesium nitrate to 16.6 g of silver oxalate and further adding purified water thereto to form a uniform solution, impregnating the completed carrier with the solution over a water bath, drying the impregnated carrier, and subjecting the dried carrier to an activating treatment in a current of air at 200° C. for 10 minutes and at 400° C. for 10 minutes.

Gas phase oxidation of ethylene was carried out by using the catalyst in the same manner as in Example 1 and the reaction was tested to determine the selectivity of the reaction for ethylene oxide. The results were as shown in Table 1.

EXAMPLE 10

A silver catalyst was obtained by impregnating 100 g of a complete carrier produced by following the procedure of Example 2 with a uniform solution formed of 30 g of silver oxalate, 16 ml of ethylene diamine, 0.244 g of cesium nitrate, and 25 ml of purified water over a water bath, drying the impregnated carrier, and subjecting the dried carrier to an activating treatment performed in a current of air at 200° C. for 10 minutes and at 400° C. for 10 minutes.

Gas phase oxidation of 1,3-butadiene was carried out by using the catalyst and the reaction was tested to determine the selectivity of this reaction for 3,4-epoxy-1-butene. To implement this reaction, a reaction vessel measuring 7.5 mm in inside diameter was packed with the catalyst pulverized in advance to a particle diameter of 0.85–1.2 mm and a reaction gas composed of 18 vol. % of oxygen, 9 vol. % of 1,3-butadiene, 5 ppm of ethylene chloride, and the balance of n-butane as a ballast gas was passed through the reaction vessel and allowed to undergo such a reaction under a pressure of 50 kPa gauge at a space velocity of 6000 $hr^{-1}$ as to set the degree of conversion of 1,3-butadiene at 40%. The treated gas was assayed to determine the selectivity of the reaction for 3,4-epoxy-1-butene. The results were as shown in Table 1.

Control 1

Gas phase oxidation of ethylene was carried out by following the procedure of Example 1 while omitting the addition of antimony to the alumina carrier having α-alumina as a main component and the heat treatment and the reaction was tested to determine the selectivity of the reaction for ethylene oxide. The results were as shown in Table 1.

Control 2

Gas phase oxidation of ethylene was carried out by following the procedure of Example 1 while using as the mixture of gases for the heat treatment a mixture of 12 vol. % of oxygen gas and 88 vol. % of nitrogen gas in the place of the mixture of hydrogen gas and nitrogen gas and the reaction was tested to determine the selectivity of the reaction for ethylene oxide. The results were as shown in Table 1.

Control 3

Gas phase oxidation of ethylene was carried out by following the procedure of Example 2 while using as the mixture of gases for the heat treatment a mixture of 12 vol. % of oxygen gas and 88 vol. % of nitrogen gas in the place of the mixture of hydrogen gas and nitrogen gas and the reaction was tested to determine the selectivity of the reaction for ethylene oxide. The results were as shown in Table 1.

Control 4

Gas phase oxidation of ethylene was carried out by following the procedure of Example 2 while omitting the heat treatment of the carrier precursor in the mixture of hydrogen gas and nitrogen gas and the reaction was tested to determine the selectivity of the reaction for ethylene oxide. The results were as shown in Table 1.

Control 5

A silver catalyst was produced by effecting deposition of silver in the same manner as in Example 10 while omitting the addition of antimony sol during the preparation of the carrier precursor. Gas phase oxidation of 1,3-butadiene was carried out by using the silver catalyst in the same manner as in Example 10 and the reaction was tested to determine the selectivity of this reaction for 3,4-epoxy-1-butene. The reaction conditions were the same as those of Example 10 except the concentration of 1,3-butadiene was set at 17% and the degree of conversion at 17%. The results were as shown in Table 1.

Control 6

Silver was deposited to produce a silver catalyst by following the procedure of Example 10 while omitting the heat treatment performed in the current of the mixture of 4 vol. % of hydrogen gas and 96 vol. % of nitrogen gas and gas phase oxidation of 1,3-butadiene was carried out by using the silver carrier in the same manner as in Control 5 and the reaction was tested to determine the selectivity of the reaction for 3,4-epoxy-1-butene. The activity was low and the specified degree of conversion could not be reached. The results were as shown in Table 1.

Control 7

Silver was deposited to produce a silver catalyst by following the procedure of Example 10 while omitting the addition of antimony sol to the carrier precursor and the heat treatment in the current of the mixture of 4 vol. % of hydrogen gas and 96 vol. % of nitrogen gas. Further, gas phase oxidation of 1,3-butadiene was carried out by using the silver catalyst in the same manner as in Control 5 and the reaction was tested to determine the selectivity of the reaction for 3,4-epoxy-1-butene. The results were as shown in Table 1.

From the results of Table 1, it is noted that the selectivity of the reaction for ethylene oxide decreased when the oxygen concentration in the gas used for the heat treatment exceeded 10 vol. %. This means that when the heat treatment is performed in such a gas as air which has an oxygen concentration exceeding 10 vol. % (namely firing), a carrier for use in a catalyst for the production of ethylene oxide with a high selectivity and consequently a silver catalyst for the production of ethylene oxide cannot be obtained.

The entire disclosure of Japanese Patent Application No. 2002-102148 filed on Apr. 4, 2002 including specification, claims and summary are incorporated herein by reference in its entirety.

What is claimed is:

1. A carrier for the production of an epoxidation catalyst, which carrier is obtained by preparing a carrier precursor containing (a) α-alumina, (b) silicon or a compound thereof, and (c) at least one element selected from the class consisting of germanium, tin, lead, phosphorus, antimony, and bismuth or a compound thereof and subsequently subjecting said precursor to a heat treatment in a non-oxidative gas.

2. A carrier according to claim 1, wherein said non-oxidative gas is at least one member selected from the group consisting of a reducing gas, an inert gas, and a gas having an oxygen concentration of not more than 10 vol. %.

3. A carrier according to claim 2, wherein said non-oxidative gas is at least one member selected from the group consisting of hydrogen gas, carbon monoxide gas, nitrogen oxide gas, dinitrogen oxide gas, ammonia, and a mixture of such gas with an inert gas.

4. A carrier according to claim 2, wherein said inert gas is at least one member selected from the group consisting of nitrogen gas, argon gas, rare gas, carbon dioxide gas, and alkane gas.

5. A carrier according to claim 3, wherein said non-oxidative gas is a mixture of hydrogen and an inert gas.

TABLE 1

| | Completed carrier | | | Nonacid gas ($H_2/N_2$) | Reaction temperature (° C.) | Selectivity for epoxide (%) |
|---|---|---|---|---|---|---|
| | Coefficient of absorption (%) | Void content (%) | Metal content (%) | | | |
| Example 1 | 40 | 61 | Sb:0.07 | 4/96 | 231 | 81.3 |
| Example 2 | 39 | 61 | Sb:0.30 | 4/96 | 235 | 81.7 |
| Example 3 | 40 | 61 | Sb:0.07 | 1.5/98.5 | 233 | 81.0 |
| Example 4 | 39 | 60 | Ge:0.10 | 4/96 | 232 | 81.1 |
| Example 5 | 40 | 61 | Sn:0.06 | 4/96 | 233 | 80.9 |
| Example 6 | 40 | 61 | Pb:0.10 | 4/96 | 236 | 81.2 |
| Example 7 | 40 | 61 | P:0.08 | 4/96 | 235 | 81.4 |
| Example 8 | 40 | 61 | Bi:0.09 | 4/96 | 234 | 81.4 |
| Example 9 | 39 | 53 | Sb:0.06 | 4/96 | 234 | 80.9 |
| Example 10 | 39 | 61 | Sb:0.30 | 4/96 | 192 | 95 |
| Control 1 | 40 | 61 | 0 | — | 235 | 80.3 |
| Control 2 | 40 | 61 | Sb:0.07 | $O_2:N_2 = 12/88$ | 239 | 79.3 |
| Control 3 | 39 | 61 | Sb:0.32 | $O_2:N_2 = 12/88$ | 236 | 79.8 |
| Control 4 | 39 | 61 | Sb:0.34 | — | 238 | 78.9 |
| Control 5 | 40 | 61 | — | $H_2:N_2 = 4/96$ | 194 | 94 |
| Control 6 | 39 | 61 | Sb:0.34 | — | Fell short of specified ratio of addition | Fell short of specified ratio of addition |
| Control 7 | 40 | 61 | — | — | 194 | 93 |

6. A carrier according to claim 5, wherein said non-oxidative gas is a mixture of hydrogen gas having a hydrogen concentration in the range of 0.1–50 vol. % and nitrogen gas.

7. A carrier according to claim 2, wherein said non-oxidative gas is a gas having an oxygen concentration of not more than 10 vol. %.

8. A carrier according to claim 5, wherein said non-oxidative gas is a mixture of hydrogen gas having a hydrogen concentration in the range of 0.1–15 vol. % and nitrogen gas.

9. A carrier according to claim 1, wherein the heat treatment in a non-oxidative gas is carried out at a temperature in the range of 400–1700° C.

10. A carrier according to claim 1, wherein said carrier precursor contains (a) α-alumina, (b) silicon or a compound thereof, and (c) at least one element selected from the class consisting of antimony, phosphorus, and bismuth or a compound thereof.

11. A carrier according to claim 1, wherein said carrier precursor contains (a) α-alumina, (b) silicon or a compound thereof, and (c) antimony or an antimony compound.

12. A carrier according to claim 1, wherein said carrier has a BET specific surface area in the range of 0.1–10 m$^2$/g, a water absorption ratio in the range of 10–50%, an average pore diameter in the range of 0.1–5 μm, and an apparent porosity in the range of 20–80%.

13. A catalyst, comprising silver and a carrier set forth in claim 1, wherein the silver is deposited on the carrier.

14. A catalyst according to claim 13, wherein the amount of the silver is in the range of 1–30 mass %.

15. A catalyst according to claim 14, further comprising a reaction promoter, wherein the reaction promoter is a metal element selected from the group consisting of alkali metals and thallium, and is also deposited on the carrier; and the amount of the reaction promoter is 0.0001–5 mass % (calculated as $M_2O$, M being an alkali metal or thallium).

16. A method for the production of an epoxide by subjecting a corresponding unsaturated hydrocarbon having 2–4 carbon atoms to gas phase partial oxidation with a molecular oxygen-containing gas in the presence of a catalyst set forth in claim 13.

17. A carrier according to claim 2, wherein the heat treatment in a non-oxidative gas is carried out at a temperature in the range of 400–1700° C.

18. A carrier according to claim 3, wherein the heat treatment in a non-oxidative gas is carried out at a temperature in the range of 400–1700° C.

19. A carrier according to claim 4, wherein the heat treatment in a non-oxidative gas is carried out at a temperature in the range of 400–1700° C.

20. A carrier according to claim 5, wherein the heat treatment in a non-oxidative gas is carried out at a temperature in the range of 400–1700° C.

21. A carrier according to claim 6, wherein the heat treatment in a non-oxidative gas is carried out at a temperature in the range of 400–1700° C.

22. A carrier according to claim 7, wherein the heat treatment in a non-oxidative gas is carried out at a temperature in the range of 400–1700° C.

23. A carrier according to claim 8, wherein the heat treatment in a non-oxidative gas is carried out at a temperature in the range of 400–1700° C.

* * * * *